US010532970B2

(12) United States Patent
Vautravers et al.

(10) Patent No.: US 10,532,970 B2
(45) Date of Patent: Jan. 14, 2020

(54) PROCESS FOR THE PREPARATION OF ALPHA, BETA UNSATURATED ALDEHYDES BY OXIDATION OF ALCOHOLS IN THE PRESENCE OF A LIQUID PHASE

(71) Applicant: BASF SE, Ludwigshafen am Rhein (DE)

(72) Inventors: Nicolas Vautravers, Ludwigshafen am Rhein (DE); Joaquim Henrique Teles, Ludwigshafen am Rhein (DE); Andreas Keller, Ludwigshafen am Rhein (DE); Michaela Fenyn, Ludwigshafen am Rhein (DE)

(73) Assignee: BASF SE (DE)

( * ) Notice: Subject to any disclaimer, the term of this patent is extended or adjusted under 35 U.S.C. 154(b) by 0 days.

(21) Appl. No.: 16/307,540

(22) PCT Filed: Jun. 27, 2017

(86) PCT No.: PCT/EP2017/065836
§ 371 (c)(1),
(2) Date: Dec. 6, 2018

(87) PCT Pub. No.: WO2018/002040
PCT Pub. Date: Jan. 4, 2018

(65) Prior Publication Data
US 2019/0177260 A1    Jun. 13, 2019

(30) Foreign Application Priority Data

Jun. 29, 2016  (EP) .................................. 16176791
Mar. 20, 2017  (EP) .................................. 17161800

(51) Int. Cl.
| C07C 45/38 | (2006.01) |
| B01J 23/00 | (2006.01) |
| B01J 23/42 | (2006.01) |
| B01J 21/18 | (2006.01) |

(52) U.S. Cl.
CPC ............... *C07C 45/38* (2013.01); *B01J 21/18* (2013.01); *B01J 23/42* (2013.01)

(58) Field of Classification Search
CPC .................................. C07C 45/38; B01J 23/42
See application file for complete search history.

(56) References Cited

U.S. PATENT DOCUMENTS

| 4,165,342 | A  | 8/1979  | Dudeck et al. |
| 6,013,843 | A  | 1/2000  | Aquila et al. |
| 6,476,260 | B1 | 11/2002 | Herrmann et al. |
| 9,969,708 | B2 | 5/2018  | Vautravers et al. |
| 9,975,837 | B2 | 5/2018  | Schelwies et al. |
| 10,087,395 | B2 | 10/2018 | Pelzer et al. |
| 10,112,882 | B2 | 10/2018 | Thrun et al. |
| 10,144,691 | B2 | 12/2018 | Vautravers et al. |
| 10,195,598 | B2 | 2/2019  | Riedel et al. |
| 10,202,324 | B2 | 2/2019  | Vautravers et al. |
| 10,259,822 | B2 | 4/2019  | Werner et al. |
| 2017/0246620 | A1 | 8/2017 | Parvulescu et al. |
| 2017/0275225 | A1 | 9/2017 | Riedel et al. |
| 2018/0208745 | A1 | 7/2018 | Vautravers et al. |
| 2018/0215724 | A1 | 8/2018 | Gordillo et al. |
| 2018/0230117 | A1 | 8/2018 | Teles et al. |
| 2018/0230176 | A1 | 8/2018 | Puhl et al. |
| 2018/0244598 | A1 | 8/2018 | Schelwies et al. |
| 2018/0290959 | A1 | 10/2018 | Thrun et al. |
| 2018/0312458 | A1 | 11/2018 | Thrun et al. |
| 2018/0362351 | A1 | 12/2018 | Parvulescu et al. |
| 2018/0362353 | A1 | 12/2018 | Vautravers et al. |
| 2019/0040005 | A1 | 2/2019 | Dehn et al. |
| 2019/0077779 | A1 | 3/2019 | Riedel et al. |

FOREIGN PATENT DOCUMENTS

| EP | 0881206 A1 | 12/1998 |
| JP | 2010202555 A | 9/2010 |
| WO | WO-9918058 A1 | 4/1999 |
| WO | WO-2008037693 A1 | 4/2008 |
| WO | WO-2017207461 A1 | 12/2017 |
| WO | WO-2018001861 A1 | 1/2018 |
| WO | WO-2018001862 A1 | 1/2018 |
| WO | WO-2018007481 A1 | 1/2018 |
| WO | WO-2018011280 A1 | 1/2018 |
| WO | WO-2018015434 A1 | 1/2018 |
| WO | WO-2018015435 A1 | 1/2018 |
| WO | WO-2018115117 A1 | 6/2018 |
| WO | WO-2018115118 A1 | 6/2018 |
| WO | WO-2018134289 A1 | 7/2018 |
| WO | WO-2018172110 A1 | 9/2018 |

OTHER PUBLICATIONS

International Search Report for PCT/EP2017/065836 dated Sep. 25, 2017.
Written Opinion of the International Searching Authority for PCT/EP2017/065836 dated Sep. 25, 2017.
U.S. Appl. No. 16/307,450, filed Dec. 5, 2018.
U.S. Appl. No. 16/307,197, filed Dec. 5, 2018.
Anderson, R., et al., "Selective Oxidation of Alcohols to Carbonyl Compounds and Carboxylic Acids with Platinum Group Metal Catalysts", Advanced Synthesis and Catalysis, vol. 345, Issue 4, 2003, pp. 517-523.
Besson, et al., "Selective oxidation of alcohols and aldehydes on metal catalysts", Catalysis Today, vol. 57, Issue 1-2, 2000, pp. 127-141.
European Search Report for EP Patent Application No. 16176791.8, dated Sep. 12, 2016, 5 pages.
Heyns, et al., "Katalytische Oxydation von Primären and Sekundären Hydroxylverbindungen mit Sauerstoff am Platinkontakt in Flüssiger Phase : Über Katalytische Oxydationen—XIV", Tetrahedron, vol. 9, Issue 1-2, 1960, pp. 67-75.

(Continued)

*Primary Examiner* — Sikarl A Witherspoon
(74) *Attorney, Agent, or Firm* — Drinker Biddle & Reath LLP

(57) ABSTRACT

Process for the preparation of alpha, beta unsaturated aldehydes by oxidation of alcohols where the oxidant is oxygen in the presence of a catalyst comprising platinum on a support in the presence of a liquid phase which contains at least 25 weight-% water based on the total weight of the liquid phase.

22 Claims, No Drawings

(56) References Cited

OTHER PUBLICATIONS

Huang, et al., "Sustainable catalytic oxidation of alcohols over the interface between air and water", Green Chemistry, vol. 17, Issue 4, 2015, pp. 2325-2329.
Kon, et al., "Oxidation of allylic alcohols to a,β-unsaturated carbonyl compounds with aqueous hydrogen peroxide under organic solvent-free conditions", Chemical Communications, Issue 42, 2007, pp. 4399-4400.
Korovchenko, et al., "Oxidation of Primary Alcohols with Air on Carbon-Supported Platinum Catalysts for the Synthesis of Aldehydes or Acids", Catalysis Today, vol. 121, Issue 1-2, Mar. 15, 2007, pp. 13-21.
Lee, et al., "Aspects of Allylic Alcohol Oxidation—a Bimetallic Heterogeneous Selective Oxidation Catalyst", Green Chemistry, vol. 2, Issue 6, Nov. 14, 2000, pp. 279-282.
Liu, et al., "Yolk-Shell Hybrid Materials with a Periodic Mesoporous Organosilica Shell: Ideal Nanoreactors for Selective Alcohol Oxidation", Advanced Functional Materials, vol. 22, Issue 3, 2012, pp. 591-599.
Ma, et al., "Palladium Nanoparticles Confined in the Nanocages of SBA-16: Enhanced Recyclability for the Aerobic Oxidation of Alcohols in Water", Journal of Molecular Catalysis A: Chemical, vol. 331, Issue 1-2, 2010, pp. 78-85.
Ng, et al., "An efficient and reusable carbon-supported platinum catalyst for aerobic oxidation of alcohols in water", Chemical Communications, vol. 0, Issue 27, 2008, pp. 3181-3183.
Tonucci, et al., "Catalytic aerobic oxidation of allylic alcohols to carbonyl compounds under mild conditions", Green Chemistry, vol. 11, Issue 6, 2009, pp. 816-820.
Wang, et al., "Aqueous-phase aerobic oxidation of alcohols by soluble Pt nanoclusters in the absence of base", Chemical Communications, Issue 42, 2007, pp. 4375-4377.

PROCESS FOR THE PREPARATION OF ALPHA, BETA UNSATURATED ALDEHYDES BY OXIDATION OF ALCOHOLS IN THE PRESENCE OF A LIQUID PHASE

CROSS-REFERENCE TO RELATED APPLICATIONS

This application is a national stage application (under 35 U.S.C. § 371) of PCT/EP2017/065836, filed Jun. 27, 2017, which claims benefit of European Application Nos. 16176791.8, filed Jun. 29, 2016 and 17161800.2, filed Mar. 20, 2017, all of which are incorporated herein by reference in their entirety.

The present invention relates to a process for preparing alpha, beta unsaturated aldehydes, such as in particular, prenal (3-methyl-2-butenal) by oxidation of alcohols in the presence of a liquid phase. More specifically, the invention relates to a process for preparing alpha, beta unsaturated aldehydes, such as, in particular prenal (3-methyl-2-butenal) by oxidation of alcohols in the presence of a liquid phase and a catalyst, wherein the liquid phase contains at least 25 weight-% water based on the total weight of the liquid phase and the oxidant is oxygen.

TECHNICAL BACKGROUND

Prenal is an important chemical intermediate especially for the preparation of terpene-based fragrances, such as citral, and for the preparation of vitamins, such as vitamin E, and therefore is of great technical and economic importance.

The most common procedures for preparing prenal use prenol (3-methyl-2-buten-1-ol) or isoprenol (3-methyl-3-buten-1-ol) as starting compounds. Thus, EP 0 881 206 describes the oxidation of these starting compounds with oxygen in the gas phase using a silver catalyst. The selectivity of this approach could be improved by further developing the catalytic system, as disclosed e.g. in WO 2008/037693. However, in order to obtain sufficient conversion rates and selectivity it is necessary to carry out the gas phase procedure at temperatures of about 360° C. while maintaining short contact times. This is required, on the one hand, to ensure adequate reactivity and, on the other hand, to prevent decomposition reactions of the sensitive reactants and products. These conditions can only be accomplished by using expensive equipment.

Processes for preparing alpha, beta unsaturated aldehydes by oxidation in the liquid phase using organic solvents are disclosed in Tetrahedron, Vol 9 (1960), 67-75, Adv. Synth. Catal. 345 (2003), 517-523 as well as in Green Chemistry, 2 (2000), 279-282.

Chem. Commun. (2008), 3181-3183, describes the oxidation of benzylalcohol and cinnamylalcohol with oxygen in water. Catalysis Today 121 (2007), 13-21 describes the oxidation of substituted benzyl alcohols with oxygen. Chem. Commun. (2007), 4375-4377 discloses the oxidation of cinnamyl alcohol to cinnamic acid as well as the oxidation of benzyl alcohol to benzoic acid in the presence of water and oxygen. Catalysis Today 57 (2000) 127-141 describes the oxidation of 5-hydroxymethylfurfural as well as the oxidation of cinnamyl alcohol. JP 2010-202555A describes the oxidation of 3 groups of alcohols to the corresponding aldehydes in a liquid phase with oxygen as oxidant. None of these references discloses a process for the preparation of the alpha, beta unsaturated aldehydes according to the present invention.

WO 99/18058 discloses a process for the aerobic oxidation of primary alcohols, such as hexanol in the absence of solvents.

Chem. Commun. (2007) 4399-4400 describes the formation of alpha, beta unsaturated aldehydes in high yields with aqueous hydrogen peroxide as the oxidant in the presence of Pt black catalyst under organic solvent free conditions. Table 1 discloses this reaction for a list of alcohols: Entry 7 discloses the oxidation of 3-methyl-2-butenol to 3-methyl-2-butenal with 5% hydrogen peroxide as oxidant and Pt black as catalyst. 3-methyl-2-butenal is obtained with a yield of 91%. Entry 4 discloses this reaction for cinnamyl alcohol. On page 4399, left column this document expressly states the necessity of using hydrogen peroxide as oxidant: "Without the use of $H_2O_2$ (under an air atmosphere), cinnamaldehyde was obtained in only <10% yield." In footnote 12, this reference summarizes previous work: "Although the oxidation of cinnamyl alcohol to cinnamaldehyde with $O_2$ (or air) has been reported, organic solvents and/or base are necessary to achieve high yield and selectivity."

Chem. Commun. (2007) 4399-4400 is considered the closest prior art, as it discloses a process for the preparation of prenal from prenol by oxidation with aqueous hydrogen peroxide as oxidant in an aqueous liquid phase in the presence of a catalyst with a yield of 91%. It has to be noted that this reference explicitly discourages from using oxygen or air as oxidant in a process for preparing alpha, beta unsaturated aldehydes.

It was an objective of the invention to provide a simple and efficient process for preparing alpha, beta unsaturated aldehydes of formula (I), in particular prenal, which is suitable for industrial scale preparations. The process should be easy to handle, assure high yields and high selectivity of the aldehyde to be prepared, thus avoiding over-oxidation to the corresponding acid. Moreover, the use of toxic or expensive reagents should be avoided.

SUMMARY OF THE INVENTION

It has now been found that this objective is achieved by an oxidation in the presence of a catalyst and in the presence of a liquid phase, wherein the liquid phase contains at least 25 weight-% of water based on the total weight of the liquid phase, determined at 20° C. and 1 bar, and wherein oxygen is used as the oxidant.

It has surprisingly been found that the alpha, beta unsaturated aldehydes of formula (I) can be obtained with excellent yield and selectivity with the process according to the invention. The process according to the invention is further associated with a series of advantages. The process according to the invention enables the preparation of alpha, beta unsaturated aldehydes of formula (I) with high yield under mild conditions, both of temperature and pressure, while requiring only moderate to low amounts of catalyst. The process can be conducted with no or low amounts of organic solvent, thus avoiding or minimizing environmentally problematic waste streams. The process also allows a simple isolation of the desired aldehyde.

In contrast to the process described in Chem. Commun. (2007) 4399-4400, no hydrogen peroxide needs to be employed and at the same time an increase in yield is obtained.

Therefore, the present invention relates to a process for the preparation of alpha, beta unsaturated aldehydes of general formula (I)

$$(R_1)(R_2)C = C(R_3) - CHO, \qquad (I)$$

wherein $R_1$, $R_2$ and $R_3$, independently of one another, are selected from
hydrogen, $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy, aryl; $C_1$-$C_6$-alkylen, which optionally carry 1, 2, 3, or 4 identical or different substituents which are selected from $NO_2$, CN, halogen, $C_1$-$C_6$ alkoxy, ($C_1$-$C_6$-alkoxy)carbonyl, $C_1$-$C_6$ acyl, $C_1$-$C_6$ acyloxy, aryl;
by oxidation of alcohols of general formula (II)

$$(R_1)(R_2)C=C(R_3)-CH_2-OH, \qquad (II)$$

wherein $R_1$, $R_2$ and $R_3$ have the meaning as given above in the presence of a catalyst and in the presence of a liquid phase, wherein the liquid phase contains at least 25 weight-% water based on the total weight of the liquid phase, determined at a temperature of 20° C. and a pressure of 1 bar and wherein the oxidant is oxygen.

Embodiments of the invention are:

1. Process for the preparation of alpha, beta unsaturated aldehydes of general formula (I)

$$(R_1)(R_2)C=C(R_3)-CHO, \qquad (I)$$

wherein $R_1$, $R_2$ and $R_3$, independently of one another, are selected from
hydrogen, $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy, aryl; $C_1$-$C_6$-alkylen, which optionally carry 1, 2, 3, or 4 identical or different substituents which are selected from $NO_2$, CN, halogen, $C_1$-$C_6$ alkoxy, ($C_1$-$C_6$-alkoxy)carbonyl, $C_1$-$C_6$ acyl, $C_1$-$C_6$ acyloxy, aryl;
by oxidation of alcohols of general formula (II)

$$(R_1)(R_2)C=C(R_3)-CH_2-OH, \qquad (II)$$

wherein $R_1$, $R_2$ and $R_3$ have the meaning as given above in the presence of a catalyst and in the presence of a liquid phase, wherein the liquid phase contains at least 25 weight-% water based on the total weight of the liquid phase, determined at a temperature of 20° C. and a pressure of 1 bar and wherein the oxidant is oxygen.

2. Process according to any of the preceding claims, wherein an alcohol according to formula (II) is used, wherein $R_1$, $R_2$ or $R_3$, independently of one another, are selected from H or $CH_3$.

3. Process according to any of the preceding claims, wherein an alcohol according to formula (II) is used, wherein $R_1$ is H and $R_2$ and $R_3$ are $CH_3$.

4. Process according to any of the preceding claims, wherein the liquid phase contains at least 50 weight-%, preferably at least 70 weight-% water based on the total weight of the liquid phase.

5. Process according to any of the preceding claims, wherein the oxidation is carried out in the presence of a catalyst selected from the group consisting of platinum, palladium and gold.

6. Process according to any of the preceding claims, wherein the catalyst comprises platinum.

7. Process according to any of the preceding claims wherein the catalyst is on a support.

8. Process according to any of the preceding claims, wherein the oxidation is carried out at a temperature of 20° C. to 100° C., preferably at a temperature of 20° C. to 70° C.

9. Process according to any of the preceding claims, wherein the oxidation is carried out under a partial pressure of oxygen between 0.2 and 8 bar.

General Definitions

In the context of the present invention, the terms used generically are, unless otherwise stated, defined as follows:

The prefix $C_x$-$C_y$ denotes the number of possible carbon atoms in the particular case.

Alkyl and also all alkyl moieties in radicals derived therefrom, such as e.g. alkoxy, acyl, acyloxy, refers to saturated, straight-chain or branched hydrocarbon radicals having x to y carbon atoms, as denoted in $C_x$-$C_y$.

Thus the term $C_1$-$C_4$-alkyl denotes a linear or branched alkyl radical comprising from 1 to 4 carbon atoms, such as methyl, ethyl, propyl, 1-methylethyl (isopropyl), butyl, 1-methylpropyl (sec-butyl), 2-methylpropyl (isobutyl) or 1,1-dimethylethyl (tert-butyl).

The term $C_1$-$C_6$-alkyl denotes a linear or branched alkyl radical comprising 1 to 6 carbon atoms, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The term alkenyl denotes mono- or poly-, in particular monounsaturated, straight-chain or branched hydrocarbon radicals having x to y carbon atoms, as denoted in $C_x$-$C_y$, and a double bond in any desired position, e.g. $C_1$-$C_6$-alkenyl, preferably $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

The term substituents denotes radicals selected from the group consisting of $NO_2$, CN, halogen, $C_1$-$C_6$ alkoxy, ($C_1$-$C_6$-alkoxy)carbonyl, $C_1$-$C_6$ acyl, $C_1$-$C_6$ acyloxy and aryl.

The term halogen denotes in each case fluorine, bromine, chlorine or iodine, especially fluorine, chlorine or bromine.

The term alkoxy denotes straight-chain or branched saturated alkyl radicals comprising from 1 to 6 ($C_1$-$C_6$-alkoxy) or 1 to 4 ($C_1$-$C_4$-alkoxy) carbon atoms, which are bound via an oxygen atom to the remainder of the molecule, such as methoxy, ethoxy, n-propoxy, 1-methylethoxy (isopropoxy), n-butyloxy, 1-methylpropoxy (sec-butyloxy), 2-methylpropoxy (isobutyloxy) and 1,1-dimethylethoxy (tert-butyloxy).

The term ($C_1$-$C_6$-alkoxy)carbonyl denotes alkoxy radicals having from 1 to 6 carbon atoms which are bound via a carbonyl group to the remainder of the molecule. Examples thereof are methoxycarbonyl, ethoxycarbonyl, propoxycarbonyl, isopropoxycarbonyl, n-butoxycarbonyl, sec-butoxycarbonyl, isobutoxycarbonyl and tert-butoxycarbonyl, n-pentyloxycarbonyl and n-hexyloxycarbonyl.

The term $C_1$-$C_6$ acyl denotes straight-chain or branched saturated alkyl radicals comprising from 1 to 6 carbon atoms, which are bound via a carbonyl group to the remainder of the molecule. Examples thereof are formyl, acetyl, propionyl, 2-methylpropionyl, 3-methylbutanoyl, butanoyl, pentanoyl, hexanoyl.

The term $C_1$-$C_6$ acyloxy denotes $C_1$-$C_6$ acyl radicals, which are bound via an oxygen atom to the remainder of the molecule. Examples thereof are acetoxy, propionyloxy, butanoyloxy, pentanoyloxy, hexanoyloxy.

The term aryl denotes carbocyclic aromatic radicals having from 6 to 14 carbon atoms. Examples thereof comprise phenyl, naphthyl, fluorenyl, azulenyl, anthracenyl and phenanthrenyl. Aryl is preferably phenyl or naphthyl, and especially phenyl.

Selectivity is defined as the number of moles of the alpha, beta unsaturated aldehyde of the general formula (I) formed divided by the number of moles of the alcohol of the general formula (II) that were consumed. The amounts of alpha, beta unsaturated aldehyde of the general formula (I) formed and starting compounds consumed can easily be determined by a GC analysis as defined in the experimental section.

PREFERRED EMBODIMENT OF THE INVENTION

The remarks made below regarding preferred embodiments of the starting compounds and the process according to the invention, especially regarding preferred meanings of the variables of the different reactants and products and of the reaction conditions of the process, apply either taken alone or, more particularly, in any conceivable combination with one another.

Starting Compounds (Reactants)

In a preferred embodiment of the invention alcohols of general formula (II) are used, wherein $R_1$, $R_2$ and $R_3$, independently of one another, are selected from the group consisting of H, $C_1$-$C_6$-alkyl and $C_1$-$C_6$-alkylen.

In a preferred embodiment of the invention alcohols of general formula (II) are used, wherein $R_3$ is H.

In a preferred embodiment of the invention alcohols of general formula (II) are used, wherein $R_1$, $R_2$ and $R_3$, independently of one another, are selected from the group consisting of H, $C_1$-$C_4$-alkyl and $C_2$-$C_6$-alkylen.

In a preferred embodiment of the invention alcohols of general formula (II) are used, wherein $R_1$, $R_2$ and $R_3$, independently of one another, are selected from the group consisting of H, $CH_3$ and $C_2H_5$.

In a preferred embodiment of the invention alcohols of general formula (II) are used, wherein $R_1$, $R_2$ and $R_3$, independently of one another, are selected from the group consisting of H and $CH_3$.

In a preferred embodiment of the invention an alcohol of the general formula (II) is used, wherein $R_1$ is H and $R_2$ and $R_3$ are $CH_3$.

In a preferred embodiment of the invention an alcohol of the general formula (II) is used, wherein $R_3$ is H and $R_2$ and $R_1$ are $CH_3$ (=3-Methyl-2-buten-1-ol, prenol).

In a preferred embodiment of the invention an alcohol of the general formula (II) is used, wherein $R_1$ is $CH_3$, $R_3$ is H and $R_2$ is $C_6$-Alkenyl, preferably 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Process

In the context of the present invention the reaction mixture consists of all components of the reaction, e.g. reactant(s), water, catalyst(s), $O_2$ and any other optional component(s), such as e.g. solvent(s).

It has surprisingly been found that the process according to the invention can be performed in the presence of a liquid phase, wherein the liquid phase contains at least 25 weight-% of water based on the total weight of the liquid phase, determined at a temperature of 20° C. and a pressure of 1 bar.

The process according to the invention is conducted in the presence of a liquid phase. The liquid phase consists of all components of the reaction mixture which are liquid at 20° C. and a pressure of 1 bar.

Reference for determining the liquid phase is the physical state of all components at 20° C. and 1 bar pressure, even if the process according to the invention is conducted at other temperatures or pressures.

The liquid phase can consist of one or more, e.g. two or three distinct liquid phases. The number of liquid phases can be chosen by a man skilled in the art, dependent for example on the choice and concentration of the reactant(s) or on the optional solvent(s).

In one embodiment of the invention the process according to the invention can be performed in the presence of a liquid phase, which consists of one liquid phase, wherein the liquid phase contains at least 25 weight-% of water based on the total weight of the liquid phase, determined at a temperature of 20° C. and a pressure of 1 bar.

In one embodiment of the invention the process according to the invention can be performed in the presence of a liquid phase, which consists of two or three distinct liquid phases, wherein at least one distinct liquid phase contains at least 25 weight-% of water based on the total weight of this distinct liquid phase, determined at a temperature of 20° C. and a pressure of 1 bar.

In one embodiment of the invention the process according to the invention can be performed in the presence of a liquid phase, which consists of two or three distinct liquid phases, wherein each distinct liquid phase contains at least 25 weight-% of water based on the total weight of this distinct liquid phase, determined at a temperature of 20° C. and a pressure of 1 bar.

In one embodiment of the invention the process according to the invention can be performed in the presence of a liquid phase, which consists of more than one distinct liquid phase, wherein at least one distinct liquid phase contains at least 25 weight-% of water based on the total weight of this distinct liquid phase, determined at a temperature of 20° C. and a pressure of 1 bar.

In one embodiment of the invention the process according to the invention can be performed in the presence of a liquid phase, which consists of more than one distinct liquid phase, wherein each distinct liquid phase contains at least 25 weight-% of water based on the total weight of this distinct liquid phase, determined at a temperature of 20° C. and a pressure of 1 bar.

The water content of a liquid phase can for example be adjusted by adding water (e.g. if a liquid phase is an aqueous phase) or by adding water and/or solvents and/or solubilizers (e.g. if a liquid phase is a non-aqueous phase, e.g. comprising reactant(s) not dissolved in the aqueous phase).

The following preferred ranges for the water content of a liquid phase apply for the at least one or each distinct liquid phase accordingly.

In a preferred embodiment of the invention the process is performed in a liquid phase, which contains at least 30 weight-%, preferably at least 40 weight-%, more preferably at least 50 weight-% of water. In a further embodiment the process can be performed in a liquid phase, which contains at least 60 weight-%, preferably at least 70 weight-%, more preferably at least 80 weight-%, more preferably at least 90 weight-%, more preferably at least 95 weight-% of water. According to one embodiment of the invention, the process can be performed in a liquid phase which contains 99.5 weight-% of water. All weight-% of water are based on the total weight of the liquid phase (or the at least one or each distinct liquid phase in case more than one liquid phase is present).

In one embodiment of the invention each distinct liquid phase contains at least 25 weight-% of water based on the total weight of this distinct liquid phase. The weight-% of water are determined at a temperature of 20° C. and a pressure of 1 bar.

Each distinct liquid phase of the reaction mixture can further comprise one or more solvent(s). Suitable solvents can be chosen depending e.g. on the starting compounds (reactants) and reaction conditions.

In a preferred embodiment a solvent is selected which has a water solubility of greater 150 g/L at 20° C. In a preferred embodiment a solvent is selected which has a vapour pressure of below 100 mbar at 20° C.

Suitable solvents are for example protic or aprotic solvents.

In a preferred embodiment one or more solvent(s) are selected from the group consisting of diethylene glycol dimethyl ether, triethylene glycol dimethylether and dimethylacetamide, polyoxymethylene dimethylether of general formula (III) $H_3C$—O—$(CH_2O)_n$—$CH_3$ wherein n=3 to 8, dimethyloxalate, methoxyacetic acid methyl ester, ethylene carbonate, propylene carbonate, ethylene glycol diacetate and diethylene glycol diacetate.

In a preferred embodiment of the process according to the invention, the reactants are present in the reaction mixture from 1 to 75 weight %, preferably 1 to 50 weight-% based on the total weight of the liquid phase, preferably from 2 to 45 weight-% based on the total weight of the liquid phase, more preferably from 3 to 40 weight-% based on the total weight of the liquid phase.

In case the liquid phase consists of more than one distinct phase, the reactants are preferably present in the reaction mixture from 1 to 75 weight-%, preferably 1 to 50 weight-% based on the total weight of one distinct liquid phase, preferably from 2 to 45 weight-% based on the total weight of one distinct liquid phase, more preferably from 3 to 40 weight-% based on the total weight of one distinct liquid phase.

In case the liquid phase consists of more than one distinct phase, the reactants are preferably present in the reaction mixture from 1 to 75 weight-%, preferably 1 to 50 weight-% based on the total weight of each distinct liquid phase, preferably from 2 to 45 weight-% based on the total weight of each distinct liquid phase, more preferably from 3 to 40 weight-% based on the total weight of one distinct liquid phase.

It has surprisingly been found that the process according to the invention can be performed with oxygen as oxidant. Oxygen can be used undiluted or diluted. The oxygen can be diluted with other inert gases like $N_2$, Ar or $CO_2$, e.g in the form of air. In a preferred embodiment of the invention oxygen is used undiluted.

The process according to the invention can be performed under pressure, preferably under a pressure above 1 bar and 15 bar.

In one embodiment of the invention the process is performed using a partial pressure of $O_2$ between 0.1 and 15 bar, preferably between 0.2 and 8 bar, more preferably between 0.2 and 5 bar and even more preferably between 1 and 4 bar.

The process according to the invention is carried out in the presence of a catalyst. Suitable catalytic systems for the process according to the invention comprise catalytically active metals, selected from the group consisting of platinum, palladium and gold.

In a preferred embodiment of the invention platinum is used as catalyst.

The catalytically active metal can be used in any form, e.g. unsupported or on a support. In a preferred embodiment the catalytically active metal is used on a support. The catalyst can optionally comprise so called promotors, which enhance the activity of the catalytically active metal. Examples for such promotors are bismuth (Bi), antimony (Sb), lead (Pb), cadmium (Cd), tin (Sn) or tellurium (Te). The promotors can for example be present on or in the support or can be added separately to the process.

In one embodiment of the invention, the process is conducted as a batch process and the molar ratio of the catalytically active metal to the alcohol of general formula (II) is in the range 0.0001:1 to 1:1, more preferably in the range 0.001:1 to 0.1:1 and even more preferably in the range 0.001:1 to 0.01:1.

In one embodiment of the invention, the process is conducted as a continuous process and the catalyst load (defined as total amount of reactant/total amount of catalytically active metal in the reactor/time unit) is in the range 0.01 to 100 g of alcohol of general formula (II) per g of catalytically active metal per hour, more preferably in the range 0.1 to 20 g of alcohol of general formula (II) per g of catalytically active metal per hour.

In case the catalytically active metal is used on a support, the support can for example be a powder, a shaped body or a mesh of iron-chromium-aluminium (FeCrAl) alloy, that was tempered in the presence of oxygen (commercially available under the trademark Kanthal®).

In a preferred embodiment of the invention the catalytically active metal (preferably platinum) is employed on a support. In a preferred embodiment the catalytically active metal (preferably platinum) is employed on a support and the support is selected from the group consisting of powders and shaped bodies.

Suitable support materials are for example carbonaceous or oxidic materials. A preferred carbonaceous support is activated carbon. The surface area of carbonaceous support materials preferably is at least 200 $m^2/g$, preferably at least 300 $m^2/g$. In case a carbonaceous support is used an activated carbon with a surface area of at least 300 $m^2/g$ is preferred. In a preferred embodiment the catalytically active metal (preferably platinum) is employed on an activated carbon support, preferably with an active carbon support with a surface area of at least 300 $m^2/g$.

In case an oxidic support is used, the oxides of the following elements can be used: Al, Si, Ce, Zr, Ti, V, Cr, Zn, Mg. The invention also encompasses the use of mixed oxides comprising two or more elements. In one embodiment of the invention mixed oxides are used as support selected from the group consisting of (Al/Si), (Mg/Si) and (Zn/Si) mixed oxides. In a preferred embodiment an oxidic support is used, selected from the group consisting of aluminum oxide or silcium dioxide. Preferably the oxidic supports have a BET-surface area of at least 1 $m^2/g$, preferably at least 10 $m^2/g$, more preferably of at least 30 $m^2/g$, more preferably of at least 50 $m^2/g$, more preferably of at least 75 $m^2/g$, especially preferred of at least 200 $m^2/g$.

In one embodiment the catalyst is selected from the group consisting of platinum on a support, wherein the support is selected from carbonaceous and oxidic materials, and wherein the oxide is selected from the group consisting of oxides of the elements selected from the group consisting of Al, Ce, Zr, Ti, V, Cr, Zn and Mg.

In one embodiment the catalyst is selected from the group consisting of platinum on a support, wherein the support is selected from carbonaceous materials and oxidic materials, and wherein the oxide is selected from the group consisting of oxides of the elements selected from the group consisting of Al, Ce, Zr and Ti.

In a preferred embodiment the catalyst is selected from the group consisting of platinum on carbon (Pt/C) and platinum on aluminium oxide (Pt/$Al_2O_3$).

In case the catalytically active metal is on a support, the content of the catalytically active metal on the support usually is in the range of 0.1 to 20 wt.-%, preferably 0.1 to 15 wt.-%, preferably in the range of 0.5 to 10 wt.-%.

The process according to the invention can be performed in reaction vessels customary for such reactions, the reaction being configurable in a continuous, semi-batch or batchwise mode. In general, the particular reactions will be performed under atmospheric pressure. The process may, however, also be performed under reduced or increased pressure.

The process according to the invention can be performed under pressure, preferably under a pressure between above 1 bar and 15 bar (absolute), preferably between above 1 bar and 10 bar (absolute). The process according to the invention can be performed at a partial pressure of oxygen from 0.1 to 15 bar, preferably from 0.2 to 10 bar, preferably from 0.2 to 8 bar, more preferably from 0.2 to 5 bar, more preferably from 1 to 3, preferably from 1 to 2.5, more preferably from 1.2 to 2 bar.

In a preferred embodiment of the invention, the process according to the invention is performed at a pressure from 1 to 3, preferably from 1 to 2.5, more preferably from 1.2 to 2 bar.

In a preferred embodiment of the invention the process is conducted as a batch process. In a preferred embodiment of the invention the process is conducted as a semi-batch process. In a preferred embodiment of the invention the process is conducted as a continuous process.

In a preferred embodiment of the invention the process in conducted with a fixed-bed catalyst. In case the process according to the invention is conducted with a fixed-bed catalyst, suitable fixed-bed reactors can be selected from the group consisting of trickle-bed reactors, bubble-packed reactors, multi-tubular reactors and plate reactors.

The process according to the invention can be conducted in one fixed-bed reactor or can preferably be conducted in more than one, preferably more than two, more preferably more than three, preferably three to five fixed-bed reactors. The one or more fixed-bed reactors can be arranged in series.

The process according to the invention can be conducted in one or more fixed-bed reactor(s) with or without heat exchange. In one embodiment of the invention, the fixed-bed reactor(s) can be operated so that a constant temperature is held over one, some or all fixed-bed reactors. In one embodiment of the invention, the fixed-bed reactor(s) can be operated so that a defined temperature gradient is maintained over one, some or all fixed-bed reactors without heat addition or removal. In one embodiment of the invention, the fixed-bed reactor(s) can be operated with a temperature controlled profile, wherein a defined temperature profile is maintained over one, some or all fixed-bed reactors with internal or external heat addition or removal.

In a preferred embodiment of the invention the process is conducted in a trickle-bed reactor with a fixed-bed catalyst. In one embodiment of the invention, the process is conducted with more than one, preferably more than two, more preferably more than three trickle-bed reactors, which are arranged in series. In one embodiment, the process is conducted with three to five trickle-bed reactors, which are arranged in series. In one embodiment, one or more, preferably each of the trickle-bed reactors can be provided with a liquid recycle stream.

In a preferred embodiment of the trickle-bed reactor, the components of the reaction can be inserted to the reactor concurrently, meaning that the liquid phase(s) and the gas phase comprising the oxidant oxygen, are inserted to the reactor at the same side, preferably at the top of the reactor.

In one embodiment of the invention the process is conducted in a bubble-packed reactor with a fixed-bed catalyst. In one embodiment of the invention, the process is conducted with more than one, preferably more than two, more preferably more than three bubble-packed reactors, which are arranged in series. In one embodiment, the process is conducted with three to five bubble-packed reactors, which are arranged in series.

In one embodiment of the bubble-packed reactor, the components of the reaction can be inserted in the reactor concurrently, meaning that the liquid phase(s) and the gas phase comprising the oxidant oxygen, are inserted to the reactor at the same side, preferably at the bottom of the reactor. In one embodiment of the bubble-packed reactor, the components of the reaction can be inserted in the reactor countercurrently, meaning that the liquid phase(s) and the gas phase comprising the oxidant oxygen, are inserted to the reactor at opposite sides. In one embodiment, the liquid phase(s) are inserted to the reactor at the bottom of the reactor, whereas the gas phase comprising oxygen as oxidant is inserted at the top of the reactor. In one embodiment, the liquid phase(s) are inserted to the reactor at the top of the reactor, whereas the gas phase comprising oxygen as oxidant is inserted at the bottom of the reactor.

In a preferred embodiment of the invention the process is conducted as a slurry process. The process can be conducted in a slurry-based system as stirred tank reactor or slurry bubble column.

The reaction is carried out by contacting the components of the reaction mixture, that is reactants (=starting compounds), i.e. alcohol(s) of general formula (II), water, catalyst, the oxidant and optional components, such as e.g. one or more solvent(s), under suitable reaction conditions.

The components of the reaction mixture can in principle be contacted with one another in any desired sequence. For example, the alcohol of general formula (II), if appropriate dissolved in water or a solvent or in dispersed form, can be initially charged and admixed with the catalyst or, conversely, the catalytic system can be initially charged and admixed with the alcohol of general formula (II) and water. Alternatively, these components can also be added simultaneously to the reaction vessel.

As an example for a batch-wise slurry process a stirred tank reactor can be used where the catalyst (e.g. Pt as a powder), the starting compound (e.g. prenol), water and optionally one or more solvent(s) are loaded. The reactor is then pressurized with oxygen. The reaction is then performed until the desired conversion is achieved.

As an example for a batch-wise slurry process a stirred tank reactor can be used where the catalyst (e.g. Pt as a powder), the starting compound (e.g. prenol) if appropriate dissolved in water or a solvent or in dispersed form, water and optionally one or more solvent(s) are loaded. The reactor is then pressurized with oxygen. The reaction is then performed until the desired conversion is achieved.

As an example for a semi-batch process a stirred tank reactor can be used where the catalyst (e.g. Pt catalyst), the starting compound (e.g. prenol) water and optionally one or more solvent(s) and are loaded. The $O_2$ is then continuously fed to the reactor until the desired conversion is achieved. As another example for a semi-batch process a fixed bed catalyst in a trickle-bed reactor can be used. The solution of starting compound (e.g. prenol), water, optionally comprising one or more solvent(s), are then pumped in a loop over the catalyst, while the $O_2$ is passed as a continuous stream through the reactor. In one embodiment of the invention the $O_2$ can be added in excess, the excess being released to the off gas, alternatively the $O_2$ can be added in an amount required to replenish the consumed $O_2$.

As an example for a continuous slurry process, a continuous stirred tank reactor can be used in which the catalyst is present. The solution of the starting compound (e.g. prenol), water, optionally comprising one or more solvent(s) and $O_2$ are added continuously. $O_2$ can be added in excess, off-gas can then be taken out continuously. In an alternative embodiment $O_2$ can be added in an amount to replenish the consumed $O_2$. The liquid reaction product can be taken off continuously through a filter in order to keep the catalyst in the reactor.

In a further example for a continuous fixed bed process, both the solution of prenol and the $O_2$ are continuously fed to a trickle bed reactor containing the catalyst. It this case it is possible to partly or fully recycle the gas and/or the liquid back to the reactor in order to achieve the desired conversion of prenol and/or $O_2$.

In a preferred embodiment, the process according to the invention is carried out in a continuous mode.

It has surprisingly been found that the process of the invention leads to selectivities of the alpha, beta unsaturated aldehyde (based on the alcohol of general formula (II)) in the range of over 90%, preferably over 93%, preferably over 95%, preferably over 97% more preferably over 99%.

Preferably the process according to the invention is conducted until a conversion of the alcohol of general formula (II) in the range of 10 to 99.99%, preferably in the range of 30 to 95%, and most preferably in the range of 50 to 80% is obtained.

Preferably the process according to the invention is performed at a temperature in the range from 1 to 250° C., preferably in the range from 5 to 150° C., preferably in the range from 20 to 100° C., more preferably in the range from 25° C. to 80° C., preferably in the range from 30 to 70° C. and more preferably in the range of 35 to 50° C. In one embodiment of the invention, the process is performed at a temperature in the range of 40 to 80° C.

The obtained crude product may be subjected to conventional purification measures, including distillation or chromatography or combined measures. Suitable distillation devices for the purification of the compounds of formula (I) include, for example, distillation columns, such as tray columns optionally equipped with bubble cap trays, sieve plates, sieve trays, packages or filler materials, or spinning band columns, such as thin film evaporators, falling film evaporators, forced circulation evaporators, wiped-film (Sambay) evaporators, etc. and combinations thereof.

The invention is further illustrated by the following non-limiting examples.

EXAMPLES

Gas Chromatographic Analysis

GC-system and separation method:
GC-system: Agilent 7890A
GC-Column: RTX-200 (60 m (Length), 0.32 mm (ID), 1.0 μm (Film))
Temperature program: 10 minutes at 60° C., 60° C. to 280° C. in 6° C./min, 10 minutes at 280° C.

Examples 1 and 2: Oxidation of Alcohols in Water at 40° C. with $O_2$ on Powdered Platinum Supported on Carbon Under Atmospheric $O_2$ Pressure A 1.6 L glass reactor, flushed three times with $O_2$, was charged with a 5 w/w. % alcohol (reactant) mixture in water (700 g) and powdered platinum on carbon (0.5 mol-% platinum based on reactant) and heated to 40° C. $O_2$ (4 l/h) was bubbled through the stirred reaction mixture for 6 hours. The mixture was then filtered and the filtrate was quantitatively analyzed by GC using dioxane as internal standard. Conversion and selectivity are based on the weight percentages of all detected components as determined by GC.

Pt/C (5 w/w.-% platinum on carbon) was obtained from Sigma-Aldrich. 3-Methyl-2-buten-1-ol ("Prenol") (99.3 w/w.-%) was obtained from BASF. (2E)-2-Methyl-2-buten-1-ol ("Tiglyl alcohol") (94 w/w.-%) was obtained from Interchim.

| Example | Alcohol | Conversion | Selectivity to aldehyde based on starting alcohol/% |
|---|---|---|---|
| Example 1 | 3-Methyl-2-butenol (prenol) | 99 | 99 |
| Example 2 | (2E)-2-Methyl-2-buten-1-ol (Tiglyl alcohol) | 79 | 99 |

With the process according to the invention, 3-Methyl-2-buten-1-al (prenal) could surprisingly be obtained at a yield of 98%, which is substantially higher than the yield obtained in the prior art process according to Chem. Commun. (2007) 4399-4400 (yield of 91%).

Example 3: Recovery of Catalyst

The powdered Pt/C catalyst used for the prenol oxidation in example 1 was recovered by filtration and reused 5 times without any loss of activity and/or selectivity.

Example 4: Oxidation of Prenol at 40° C. with $O_2$ on Powdered Platinum Supported on Carbon Under $O_2$ Pressure in Water A 270 mL autoclave was charged with a 5 w/w.-% prenol solution in water (120 g) and powdered platinum on carbon (0.5 mol-% platinum based on prenol). The autoclave was flushed with $N_2$, pressurized to 3 bar $N_2$ and heated to 40° C. The $N_2$ pressure was then released and the autoclave pressurized with 2 bar $O_2$; the gas volume was then flushed three times with $O_2$. The pressure was held constant for 3 hours at 40° C. over the stirred reaction mixture. The reactor was then depressurized, the solution filtered and the filtrate analyzed by GC using dioxane as internal standard. Conversion and selectivity are based on the weight percentages of all detected components as determined by GC.

Example 5: Oxidation of Prenol at 40° C. with $O_2$ on Powdered Platinum Supported on Carbon Under $O_2$ Pressure in a Water/Bis(2-Methoxyethyl)Ether Mixture A 270 mL autoclave was charged with a 17 w/w. % prenol solution in a water/bis(2-methoxyethyl)ether mixture (80/20 w/w-%) (120 g) and powdered platinum on carbon (0.5 mol-% platinum based on prenol). The autoclave was flushed with $N_2$, pressurized to 3 bar $N_2$ and heated to 40° C. The $N_2$ pressure was then released and the autoclave pressurized with 2 bar $O_2$; the gas volume was then flushed three times with $O_2$. The pressure was held constant for 3 hours at 40° C. over the stirred reaction mixture. The reactor was then depressurized, the solution filtered and the filtrate analyzed by GC using dioxane as internal standard. Conversion and selectivity are based on the weight percentages of all detected components as determined by GC.

Pt/C (5 w/w. % platinum on carbon) was obtained from Sigma-Aldrich. Prenol (99.3 w/w. %) was obtained from BASF. Bis(2-methoxyethyl)ether (Diglyme) was obtained from Sigma-Aldrich.

| Example | Solvent | Conversion | Selectivity to aldehyde based on starting alcohol/% |
|---|---|---|---|
| Example 4 | Water | 99 | 99 |
| Example 5 | Water/bis(2-methoxyethyl)ether | 95 | 99 |

The invention claimed is:

1. A process for the preparation of alpha, beta unsaturated aldehydes of general formula (I)

$$(R_1)(R_2)C\!=\!\!C(R_3)\!-\!\!CHO, \qquad (I)$$

wherein $R_1$, $R_2$ and $R_3$, independently of one another, are selected from the group consisting of H, $CH_3$ and $C_2H_5$ and wherein $R_3$ is H,
by oxidation of alcohols of general formula (II)

$$(R_1)(R_2)C\!=\!\!C(R_3)\!-\!\!CH_2\!-\!\!OH, \qquad (II)$$

wherein $R_1$, $R_2$ and $R_3$ have the meaning as given above in the presence of a catalyst and in the presence of a liquid phase, wherein the liquid phase contains at least 25 weight-% water based on the total weight of the liquid phase, determined at a temperature of 20° C. and a pressure of 1 bar and wherein the oxidant is oxygen, and wherein the catalyst comprises platinum on a support and
the alpha, beta unsaturated aldehyde has a selectivity (based on the alcohol of general formula (II)) in the range of over 90%.

2. The process according to claim 1, wherein an alcohol according to formula (II) is used, wherein $R_3$ is H and $R_2$ and $R_1$ are $CH_3$.

3. The process according to claim 1, wherein the liquid phase contains at least 50 weight-% water based on the total weight of the liquid phase.

4. The process according to claim 1, wherein the oxidation is carried out at a temperature of 20° C. to 100° C.

5. The process according to claim 1, wherein the oxidation is carried out under a partial pressure of oxygen between 0.2 and 8 bar.

6. The process according to claim 2, wherein the liquid phase contains at least 50 weight % water based on the total weight of the liquid phase.

7. The process according to claim 1, wherein the liquid phase contains at least 70 weight % water based on the total weight of the liquid phase.

8. The process according to claim 2, wherein the liquid phase contains at least 70 weight % water based on the total weight of the liquid phase.

9. The process according to claim 2, wherein the oxidation is carried out at a temperature of 20° C. to 100° C.

10. The process according to claim 3, wherein the oxidation is carried out at a temperature of 20° C. to 100° C.

11. The process according to claim 1, wherein the oxidation is carried out at a temperature of 20° C. to 70° C.

12. The process according to claim 2, wherein the oxidation is carried out at a temperature of 20° C. to 70° C.

13. The process according to claim 3, wherein the oxidation is carried out at a temperature of 20° C. to 70° C.

14. The process according to claim 8, wherein the oxidation is carried out at a temperature of 20° C. to 70° C.

15. The process according to claim 2, wherein the oxidation is carried out under a partial pressure of oxygen between 0.2 and 8 bar.

16. The process according to claim 14, wherein the oxidation is carried out under a partial pressure of oxygen between 0.2 and 8 bar.

17. The process according to claim 1, wherein said catalyst comprises a promotor, which enhance the activity of the catalytically active metal.

18. The process according to claim 1, wherein said promotor is bismuth (Bi), antimony (Sb), lead (Pb), cadmium (Cd), tin (Sn) or tellurium (Te).

19. The process according to claim 1, wherein the alpha, beta unsaturated aldehyde has a selectivity (based on the alcohol of general formula (II)) in the range of over 93%.

20. The process according to claim 1, wherein the alpha, beta unsaturated aldehyde has a selectivity (based on the alcohol of general formula (II)) in the range of over 95%.

21. The process according to claim 1, wherein the alpha, beta unsaturated aldehyde has a selectivity (based on the alcohol of general formula (II)) in the range of over 97%.

22. The process according to claim 1, wherein the alpha, beta unsaturated aldehyde has a selectivity (based on the alcohol of general formula (II)) in the range of over 99%.

* * * * *